(12) United States Patent
Mooberry et al.

(10) Patent No.: US 7,435,754 B2
(45) Date of Patent: *Oct. 14, 2008

(54) LAULIMALIDE MICROTUBULE STABILIZING AGENTS

(75) Inventors: Susan L. Mooberry, San Antonio, TX (US); Bradley S. Davidson, River Heights, UT (US)

(73) Assignees: Utah State University, Logan, UT (US); University of Hawaii, Honolulu, HI (US)

( * ) Notice: Subject to any disclaimer, the term of this patent is extended or adjusted under 35 U.S.C. 154(b) by 1063 days.

This patent is subject to a terminal disclaimer.

(21) Appl. No.: 10/126,674

(22) Filed: Apr. 19, 2002

(65) Prior Publication Data

US 2002/0198256 A1 Dec. 26, 2002

Related U.S. Application Data

(63) Continuation of application No. 09/493,897, filed on Jan. 28, 2000, now Pat. No. 6,414,015.

(51) Int. Cl.
*A61K 31/335* (2006.01)
*A61K 31/35* (2006.01)
*A01N 43/02* (2006.01)
*A01N 43/16* (2006.01)
(52) U.S. Cl. .................. 514/455; 514/450; 514/256
(58) Field of Classification Search ................ 514/455
See application file for complete search history.

(56) References Cited

U.S. PATENT DOCUMENTS 5,840,750 A 11/1998 Longley et al. ............. 514/459
5,948,919 A 9/1999 Sisti et al. ................... 549/510
5,965,739 A 10/1999 Kelly et al. ................. 548/215

FOREIGN PATENT DOCUMENTS

| WO | WO 97/10242 A | 3/1997 |
| WO | WO 99/01124 | 1/1999 |
| WO | WO 99/29704 | 6/1999 |
| WO | WO 99/43320 | 9/1999 |
| WO | WO 00/01682 | 1/2000 |
| WO | WO 00/10988 | 3/2000 |

OTHER PUBLICATIONS

Goodman and Gilman's The Pharmacological Basis of Therapeutics (10th edition, McGraw-Hill publishing, pp. 1381-1388).*
Quinoa et al. (Fijianolides, Polyketide Heterocycles from a Marine Sponge, J. Org. Chem. 1988, 53, 3544-3646).*
Corley et al. (J. Org. Chem., vol. 53, No. 15, 1988).*
Tanaka, Jun-ichi, et al., "New cytotoxic macrolides from the sponge *Fasciospongia rimosa*", *Chem. Lett.* (1996), (4), 255-6.
Chatgilialoglu et al., "Fijianolides, Polyketide Heterocycles from a Marine Sponge," *J. Org. Chem.*, 53:3642-3644, 1988.
Mooberry et al., "Laulimalide and Isolaulimalide, New Paclitaxel-Like Microtubule-Stabilizing Agents[1]," *Cancer Research*, 59:653-660, 1999.
Quinoa et al., "Laulimalides: New Potent Cytotoxic Marcrolides from a Marine Sponge and a Nudibranch Predator," *J. Org. Chem.*, 53:3644-3646, 1988.

* cited by examiner

*Primary Examiner*—Sreeni Padmanabhan
*Assistant Examiner*—Leonard M. Williams
(74) *Attorney, Agent, or Firm*—Foley & Lardner, LLP (57) ABSTRACT

A method of inhibiting the proliferation of a hyperproliferative mammalian cell having a multiple drug resistant phenotype utilizing an amount of a laulimalide compound effective to disrupt the dynamic state of microtubule polymerization and depolymerization to arrest cell mitosis is disclosed, together with laulimalide compounds which find use in such method.

15 Claims, 2 Drawing Sheets

LAULIMALIDE MICROTUBULE STABILIZING AGENTS

RELATED APPLICATIONS

This application is a continuation of U.S. application Ser. No. 09/493,897, filed Jan. 28, 2000 now U.S. Pat. No. 6,414,015, which is incorporated by reference herein in its entirety.

BACKGROUND OF THE INVENTION

Neoplastic diseases or cancers, characterized by the proliferation of cells not subject to normal growth regulation, are a major cause of death in humans. An estimated 1,221,800 new cases and 561,000 deaths are expected to occur in 1999. Lung cancer remains the leading cause of cancer-related deaths in the United States; the estimated 158,900 deaths would account for 28% of the total.

Clinical experience in chemotherapy has demonstrated that new and more effective cytotoxic drugs are desirable to treat these diseases. Such experience has also demonstrated that drugs which disrupt the microtubule system of the cytoskeleton can be effective in inhibiting the proliferation of neoplastic cells.

The microtubule system of eucaryotic cells is a major component of the cytoskeleton and is in a dynamic state of assembly and disassembly; that is, heterodimers of tubulin are polymerized to form microtubules, and microtubules are depolymerized to their constituent components. Microtubules play a key role in the regulation of cell architecture, metabolism, and division, and the dynamic state of the microtubules is critical to their normal function. With respect to cell division, tubulin is polymerized into microtubules that form the mitotic spindle. The microtubules are then depolymerized when the mitotic spindle's role has been fulfilled. Accordingly, agents which disrupt the polymerization or depolymerization of microtubules, and thereby inhibit cell growth, comprise some of the most effective chemotherapeutic agents in clinical use.

Such anti-mitotic agents or poisons all kinetically inhibit the normal dynamics of microtubules. There are subtle differences between certain classes of anti-microtubule agents based on their molecular mechanism of action. Colchicine binds to soluble tubulin and then is incorporated into a growing microtubule, vinblastine binds to the microtubule end and thereby suppresses microtubule dynamics. At high concentrations, both colchicine and vinblastine cause the loss of cellular microtubules. Paclitaxel (more commonly known as Taxol™) and related taxanes also inhibit microtubule dynamics, yet at high concentrations these agents cause an increase in polymerized tubulin in the cell and thick microtubule bundles are formed.

Paclitaxel was first isolated in 1971 in the bark of the Pacific yew tree (*Taxus brevifolia*), and was approved in 1992 by the US Food and Drug Administration for treatment of metastatic ovarian cancer and later for breast cancer. Paclitaxel has attracted unusually strong scientific attention, not only because of its unique anti-proliferative mechanism of action, but also because it is unique anti-tumors. The discovery of the effectiveness of the natural product paclitaxel lead to the production and testing of semisynthetic congeners including docitaxel (Taxotere). These compounds, taxanes, are now recognized as a new class of anti-cancer compounds.

One drawback of paclitaxel is its extreme insolubility: Paclitaxel can be administered effectively only in a solvent including cremophor, which combination can provoke severe hypersensitive immune responses. As a result of these drawbacks, it is considered desirable to explore the use of other naturally-occurring compounds with similar modes of action.

In addition, merely having activity as an antimitotic agent does not guarantee efficacy against a tumor cell, and certainly not a tumor cell which exhibits a drug-resistant phenotype. Vinca alkaloids, such as vinblastine and vincristine, and taxanes are effective against neoplastic cells and tumors, yet they lack or display reduced activity against drug-resistant tumors and cells. One basis for a neoplastic cell displaying drug resistance (DR) or multiple-drug resistance (MDR) is through the over-expression of P-glycoprotein. Compounds which are poor substrates for transport of P-glycoprotein should be useful in circumventing such DR or MDR phenotypes.

Accordingly, the exhibition of the DR or MDR phenotype by many tumor cells and the clinically proven mode of action of anti-microtubule agents against neoplastic cells necessitates the development of anti-microtubule agents cytotoxic to non-drug resistant neoplastic cells as well as cytotoxic to neoplastic cells with a drug resistant phenotype.

Since the discovery of the mechanism of action of paclitaxel, only three other non-taxane chemical classes (epothilones A and B, discodermolide, and eleutherobin and related sarcodictyins A and B) have been identified that possess a similar mode of action. The epothilones were isolated from the myxobacterium *Sorangium cellulosum* as a result of a large-scale screening effort. The epothilones have generated significant interest, as they retain activity against drug-resistant cell lines. Epothilones have been isolated from a species of bacteria found in soil samples collected from the banks of the Zambesi River in the Republic of South Africa, and have been recently synthesized.

Discodermolide was purified from the marine sponge *Discodermia dissoluta* as an immunosuppressant and was screened for anti-mitotic activity on the basis of a predictive structure-activity relationship when compared with other tubulin-interacting drugs. Discodermolide promotes tubulin assembly more potently than paclitaxel and it is an effective inhibitor of cell growth in paclitaxel-resistant cells.

Eleutherobin, a potent cytotoxin from the soft coral *eleutherobia* sp., promotes tubulin polymerization but exhibits cross-resistance to paclitaxel-resistant cell lines. The potential therapeutic usefulness of these new microtubule-stabilizing compounds, and whether they will provide advantages over the taxanes, have yet to be determined.

Accordingly, it remains desirable to identify additional naturally-occurring compounds with modes of action similar to the taxanes, but which display different tissue specificity, solubility, and/or activity against drug-resistant, and particularly multiple-drug resistant, tumors and cells.

DISCLOSURE OF THE INVENTION

The present invention provides a method of inhibiting the proliferation of a hyperproliferative mammalian cell having a multiple drug resistant phenotype comprising contacting the cell with an amount of a laulimalide compound effective to disrupt the dynamic state of microtubule polymerization and depolymerization to arrest cell mitosis, thereby inhibiting the proliferation of the cell.

The laulimalide compounds which find use in the present invention will have a general structure according to the following formula:

in which A and B are structural variants of Laulimalide regions A and B as follows:

and where the epoxide ring in the formula can optionally be replaced with a double bond, which variants preserve the ability to inhibit the proliferation of a hyperproliferative mammalian cell having a multiple drug resistant phenotype.

Specific embodiments of compounds which will be found useful in the practice of the present invention are represented here by laulimalide:

Laulimalide and variants know to exist in the basic laulimalide structure, including isolaulimalide, which differ structurally from laulimalide as follows:

Isolaulimalide

Furthermore, synthetic variants of the native laulimalide structure, termed analogs, which differ structurally from laulimalide as follows, are expected to retain the ability to inhibit the proliferation of a hyperproliferative mammalian cell having a multiple drug resistant phenotype:

-continued

A further aspect of the present invention includes compositions comprising the novel Laulimalide analog compounds.

Other aspects of the present invention will be readily apparent from the following more detailed description.

BRIEF DESCRIPTION OF THE DRAWINGS

The invention will be better understood by reference to the following detailed description of specific embodiments when considered in combination with the drawings that form a part of this specification, wherein:

FIG. 2 collectively is a graphic representation comparing the effects of Laulimalide on cell cycle distribution, wherein log phase growth cultures of MDA-MB-435 cells were treated, the cells were fixed, stained, and analyzed on a Coulter EPICS XL-MCL flow cytometer and plotted as events versus propidium iodide fluorescene intensity, and in which:

FIG. 3 collectively is a graphic representation comparing the effects of Laulimalide and paclitaxel on tubulin polymerization, in which the polymerization of bovine brain tubulin was monitored, and in which:

DETAILED DESCRIPTION OF THE INVENTION

The present invention provides a method of inhibiting the proliferation of a hyperproliferative mammalian cell having a multiple drug resistant phenotype comprising contacting the cell with an amount of a laulimalide compound effective to disrupt the dynamic state of microtubule polymerization and depolymerization to arrest cell mitosis, thereby inhibiting the proliferation of the cell.

The laulimalide compounds which find use in the present invention will have a general structure according to the following formula:

in which A and B are structural variants of Laulimalide regions A and B as follows:

and where the epoxide ring in the formula can optionally be replaced with a double bond, which variants preserve the ability to inhibit the proliferation of a hyperproliferative mammalian cell having a multiple drug resistant phenotype.

Specific embodiments of compounds which will be found useful in the practice of the present invention are represented here by laulimalide:

Laulimalide and variants know to exist in the basic laulimalide structure, including isolaulimalide, which differ structurally from laulimalide as follows:

Isolaulimalide

Together, with analog variants of laulimalide, including the following representative examples (wherein A and B represent regions where structural variation is permissible while retaining some measure of the activity of the title compound laulimalide):

R = CH$_2$OCH$_3$

Certain of the laulimalide compounds of the present invention were previously isolated from *Cacospongis mycofijiensis*, a marine sponge. These include Laulimalide and isolaulimalide. Generally, the native compounds are isolated as follows:

Lyophilized *C. mycofijiensis* were ground to a powder and extracted by stirring with dichloromethane/isopropanol for 24 hours at room temperature. The extraction was repeated under identical conditions with fresh solvent, and the combined extracts were evaporated in vacuo below 40° C. The residue was dissolved in 90% (v/v) aqueous methanol and extracted three times with equal volumes of hexanes, and the hexane fractions were discarded. The aqueous methanol phase was diluted with water to 80% (v/v) aqueous methanol and extracted three times with equal volumes of toluene. The combined toluene fractions were evaporated in vacuo below 40° C. to dryness. The residue was dissolved in a minimum amount of dichloromethane and applied to a silica gel column equilibrated in ether, and the column was elated with ether. Active fractions were combined and rechromatographed over silica gel using a solvent system of 75% methyl-tert-butyl ether/25% hexanes (v/v) containing 1% isopropanol.

Although somewhat laborious, the structure of the laulimalides as a class is amenable to chemical synthesis and the production of analogs, by techniques known in the art, is within the routine skill of an organic chemist. Thus, it is anticipated that laulimalide analogs can be routinely synthesized while preserving some measure of the activity of the representative members of the class of compounds and their ability to inhibit the proliferation of a hyperproliferative mammalian cell having a multiple drug resistant phenotype. Thus, novel laulimalide analogs having the following structure are also considered to be within the scope of the present invention:

R = CH$_2$OCH$_3$

-continued

In embodiments of the present invention, the method further comprises contacting the cell with at least one additional anti-neoplastic agent. In further embodiments of the invention, the mammalian cell is human.

The present invention also provides a method of alleviating a pathological condition caused by hyperproliferating, multiple drug resistant mammalian cells comprising administering to a subject an effective amount of the pharmaceutical composition disclosed herein to inhibit proliferation of the cells. In further embodiments of the present invention, the mammalian cells are human.

In certain embodiments of the present invention, the method further comprises administering to the subject at least one additional therapy directed to alleviating the pathological condition. In certain embodiments of the present invention, the pathological condition is characterized by the formation of neoplasms. In further embodiments of the present invention, the neoplasms are selected from the group consisting of mammary, small-cell lung, non-small-cell lung, colorectal, leukemia, melanoma, pancreatic adenocarcinoma, central nervous system (CNS), ovarian, prostate, sarcoma of soft tissue or bone, head and neck, gastric which includes pancreatic and esophageal, stomach, myeloma, bladder, renal, neuroendocrine which includes thyroid and non-Hodgkin's disease and Hodgkin's disease neoplasms.

The novel and the previously disclosed laulimalide compounds of the present invention can be therapeutically employed as anti-neoplastic agents and thereby used in methods to treat neoplastic diseases. As used herein, "neoplastic" pertains to a neoplasm, which is an abnormal growth, such growth occurring because of a proliferation of cells not subject to the usual limitations of growth. As used herein, "anti-neoplastic agent" is any compound, composition, admixture, co-mixture or blend with inhibits, eliminates, retards or reverses the neoplastic phenotype of a cell.

Chemotherapy, surgery, radiation therapy, therapy with biologic response modifiers, and immunotherapy are currently used in the treatment of cancer. Each mode of therapy has specific indications which are known to those of ordinary skill in the art, and one or all may be employed in an attempt to achieve total destruction of neoplastic cells. Chemotherapy utilizing one or more laulimalides is provided by the present invention. Moreover, combination chemotherapy, chemotherapy utilizing laulimalides in combination with other neoplastic agents, is also provided by the subject invention as combination therapy is generally more effective than the use of single anti-neoplastic agents. Thus, a further aspect of the present invention provides compositions containing a therapeutically effective amount of at least one new laulimalide compound of the present invention, including nontoxic addition salts thereof, which serve to provide the above-recited therapeutic benefits. Such compositions can also be provided together with physiologically tolerable liquid, gel or solid carriers, diluents, adjuvants and excipients. Such carriers, diluents, adjuvants and excipients may be found in the *United States Pharmacopeia* Vol. XXII and *National Formulary* Vol XVII, U.S. *Pharmacopeia* Convention, Inc., Rockville, Md. (1989), the contents of which are herein incorporated by reference. Additional modes of treatment are provided in *AHFS Drug Information,* 1993 ed. by the American Hospital Formulary Service, pp. 522-660, the relevant contents of which are herein incorporated by this reference.

Certain embodiments of the present invention further provide that the pharmaceutical composition used to treat neoplastic disease contains at least one laulimalide compound and at least one additional anti-neoplastic agent. Anti-neoplastic compounds which may be utilized in combination with laulimalides include those provided in *The Merck Index,* 11th ed. Merck & Co., Inc. (1989) pp. Ther 16-17, the contents of which are hereby incorporated by reference. In a further embodiment of the invention, anti-neoplastic agents may be anti-metabolites which may include, but are not limited to, methotrexate, 5-fluorouracil, 6-mercaptopurine, cytosine arabinoside, hydroxyurea, and 2-chlorodeoxyadenosine. In another embodiment of the present invention, the anti-neoplastic agents contemplated are alkylating agents which may include, but are not limited to, cyclophosphamide, melphalan, busulfan, paraplatin, chlorambucil, and nitrogen mustard. In a further embodiment of the subject invention, the anti-neoplastic agents are plant-derived natural products which may include, but are not limited to, vincristine, vinblastine, paclitaxel, and etoposide. In a further embodiment of the present invention, the anti-neoplastic agents contemplated are antibiotics which may include, but are not limited to, doxorubicin (adriamycin), daunorubicin, mitomycin c, and bleomycin. In a further embodiment of the subject invention, the anti-neoplastic agents contemplated are hormones which may include, but are not limited to, calusterone, diomostavolone, propionate, epitiostanol, mepitiostane, testolactone, tamoxifen, polyestradiol phosphate, megesterol acetate, flutamide, nilutamide, and trilotane. In a further embodiment of the subject invention, the anti-neoplastic agents contemplated include enzymes which may include, but are not limited to, L-Asparaginase or aminoacridine derivatives which may include, but are not limited to, amsacrine. Additional anti-neoplastic agents include those provided in Skeel, Roland T., "Antineoplastic Drugs and Biologic Response Modifier: Classification, Use and Toxicity of Clinically Useful Agents," *Handbook of Cancer Chemotherapy* (3rd ed.), Little Brown & Co. (1991), the relevant contents of which are herein incorporated by this reference.

The present laulimalide compounds and compositions can be administered to mammals for veterinary use, such as for domestic animals, and clinical use in humans in a manner similar to other therapeutic agents. In general, the dosage required for therapeutic efficacy will vary according to the type of use and mode of administration, as well as the particularized requirements of individual hosts. Ordinarily, dosages will range from about 0.001 to 1000 mg/kg, more usually 0.01 to 10 mg/kg, of the host body weight. Alternatively, dosages within these ranges can be administered by constant infusion over an extended period of time, usually exceeding 24 hours, until the desired therapeutic benefits have been obtained. Indeed, drug dosage, as well as route of administration, must be selected on the basis of relative effectiveness, relative toxicity, growth characteristics of tumor and effect of laulimalides on cell cycle, drug pharmacokinetics, age, sex, physical condition of the patient, and prior treatment.

The laulimalide compounds, with or without additional anti-neoplastic agents, may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Such salts may also be formed as acid addition salts with any free cationic groups and will generally be formed with inorganic acids such as, for example, hydrochloric or phosphoric acids, or organic acids such as acetic, oxalic, tartaric, mandelic, and the like. Additional excipients which the further invention provides are those available to one of ordinary skill in the art, for example, that found in the *United States Pharmacopeia* Vol. XXII and *National Formulary* Vol XVII, U.S. *Pharmacopeia* Convention, Inc., Rockville, Md. (1989), the relevant contents of which is herein incorporated by this reference.

The suitability of particular carriers for inclusion in a given therapeutic composition depends on the preferred route of administration. For example, anti-neoplastic compositions may be formulated for oral administration. Such compositions are typically prepared either as liquid solution or suspensions, or in solid forms. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%.

Compositions of the present invention may also be prepared as injectable, either as liquid solutions, suspensions, or emulsions; solid forms suitable for solution in, or suspension in, liquid prior to injection may be prepared. Such injectables may be administered subcutaneously, intravenously, intraperitoneally, intramuscularly, intrathecally, or intrapleurally. The active ingredient or ingredients are often mixed with diluents or excipients which are physiologically tolerable and compatible with the active ingredient(s). Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

The invention further provides methods for using laulimalide compounds encompassed by the genus structure to inhibit the proliferation of mammalian cells by contacting these cells with a laulimalide compound in an amount sufficient to inhibit the proliferation of the mammalian cell. A preferred embodiment is a method to inhibit the proliferation of hyperproliferative mammalian cells. For purposes of this invention, "hyperproliferative mammalian cells" are mammalian cells which are not subject to the characteristic limitations of growth, e.g., loss of growth control and insensitivity to normal programmed cell death (apoptosis). A further preferred embodiment is when the mammalian cell is human. The invention further provides contacting the mammalian cell with at least one laulimalide compound and at least one additional anti-neoplastic agent. The types of anti-neoplastic agents contemplated are the same as those disclosed hereinabove.

The invention further provides methods for using laulimalide compounds encompassed by the genus structure to inhibit the proliferation of hyperproliferative cells with drug-resistant phenotypes, including those with multiple drug-resistant phenotypes, by contacting said cell with a laulimalide compound in an amount sufficient to inhibit the proliferation of a hyperproliferative mammalian cell. A preferred embodiment is when the mammalian cell is human. The invention further provides contacting the mammalian cell with a laulimalide compound and at least one additional anti-neoplastic agent. The types of anti-neoplastic agents contemplated are the same as those disclosed hereinabove.

The invention further provides a method for alleviating pathological conditions caused by hyperproliferating mammalian cells, for example, neoplasia, by administering to a subject an effective amount of a pharmaceutical composition provided hereinabove to inhibit the proliferation of the hyperproliferating cells. As used herein "pathological condition" refers to any pathology arising from the proliferation of mammalian cells that are not subject to the normal limitations of cell growth. Such proliferation of cells may be due to neoplasms, including, but not limited to the following neoplasms: mammary, small-cell lung, non-small-cell lung, colorectal, leukemia, melanoma, central nervous system (CNS), ovarian, prostate, sarcoma of soft tissue or bone, head and neck, gastric which includes pancreatic and esophageal stomach, myeloma, bladder, renal, neuroendocrine which includes thyroid and lymphoma, non-Hodgkin's and Hodgkin's. In a further embodiment of the invention, the neoplastic cells are human. The present invention further provides methods of alleviating such pathological conditions utilizing laulimalide in combination with other therapies, as well as other antineoplastic agents. Such therapies and their appropriateness for different neoplasia may be found in *Cancer Principles and Practice of Oncology*, 4th ed., Editors DeVita, V., Hellman, S., and Rosenberg., S., Lippincott Co. (1993), the contents of which are herein incorporated by reference.

In the present disclosure, laulimalide compounds are shown to potently stabilize the microtubule structure in cultured cells. In addition, and in contrast with the Vinca alkaloids and paclitaxel, laulimalide compounds appear to be a poor substrate for the drug-efflux pump P-glycoprotein.

The following examples serve to illustrate certain embodiments and aspects of the present invention and are not to be construed as limiting the scope thereof.

Experimental

In the experimental disclosure which follows, all weights are given in grams (g), milligrams (mg), micrograms (μg), nanograms (ng), or picogmams (pg), all amounts are given in moles (mol), millimoles (mmol), micromoles (μmol), nanomoles (nmol), picomoles (pmol), or femtomoles (fmol), all concentrations are given as percent by volume (%), proportion by volume (v:v), molar (M), millimolar (mM), micromolar (μM), nanomolar (nM), picomolar (pM), femtomolar (fM), or normal (N), all volumes are given in liters (L), milliliters (mL), or microliters (μL), and linear measurements are given in millimeters (mm), or nanometers (nm) unless otherwise indicated.

The following examples demonstrate the practice of the present invention in isolating, purifying and employing laulimalide microtubule stabilizing agents for inhibiting the proliferation of a hyperproliferative mammalian cell having a multiple drug resistant phenotype.

Reagents 4,6-Diamidino-2-phenylndole (DAPI), sulforhodamine B (SRB), antibodies against β-tubulin, and Basal Medium Eagle containing Earle's salts (BME) were obtained from the Sigma Chemical Company (St. Louis, Mo.). Richter's medium was obtained from BioWhittaker (Walkersville, Md.) and Fetal Bovine Serum (FBS) was obtained from Hyclone Laboratories (Logan, Utah).

Cell Lines

The A-10 rat aortic smooth muscle and SK-OV-3 human ovarian carcinoma cell lines were obtained from the American Type Culture Collection (Manassas, Va.) and were cultured in BME containing 10% FBS and 50 μg/mL gentamycin sulfate. A sub-line of SK-OV-3 selected for resistance to vinblastine (SKVLB-1) was provided by Dr. Victor Ling (British Columbia Cancer Center, Vancouver, British Columbia) and was maintained in BME containing 10% FBS and 50 μg/mL gentamycin sulfate. The MDA-MB-435 human mammary adenocarcinoma cell line was obtained from Dr. Mai Higazi (Georgetown University, Washington, D.C.), and was maintained in Richters medium containing 10% FBS and 50 μg/mL gentamycin sulfate. Vinblastine was added to a final concentration of 1 μg/mL to SKVLB-1 cells 24 hours after passage to maintain selection pressure for P-glycoprotein-overexpressing cells.

Inhibition of Cell Proliferation

The $IC_{50}$ for inhibition of cell proliferation was determined by measuring cell-associated protein after drug treatment using the sulforhodamine B assay.

Immunofluorescence Assays

A-10 cells were grown to 70-85% confluence on glass coverslips in BME supplemented with 10% FBS. Drug compounds in PBS were added to the indicated final concentrations and cells were incubated for an additional 24 hours.

For the staining of microtubules and intermediate filaments, the cells were fixed with cold methanol for 5 minutes, blocked for 20 minutes with PBS containing 10% calf serum to block nonspecific binding sites, and incubated at 37° C. for 90 min with monoclonal anti-β-tubulin at the dilutions recommended by the manufacturer. Bound primary antibodies were subsequently visualized by a one hour incubation with fluorescein(FITC)-conjugated sheep antimouse IgG (F-3008; Sigma). The coverslips were washed, stained with 0.1 μg/mL DAPI for 10 minutes, mounted on microscope slides and the fluorescence patterns were examined and photographed using a Zeiss Axioplan microscope equipped with epifluorescence optics for fluorescein and DAPI.

Effects of Laulimalide, Isolaulimalide, and Paclitaxel on Cellular Microtubules

Strong paclitaxel-like microtubule-stabilizing activity was found in the crude lipophilic extract from the marine sponge *C. mycofijiensis*. The extract was cytotoxic, and after treatment the only cell remnants that remained where thick, short microtubule bundles. Bioassay-directed purification of the extract yielded the microtubule active-compounds laulimalide and isolaulimalide, as well as the microfilament disrupter latrunuculin A. Studies with the purified compounds show that both laulimalide and isolaulimalide caused dramatic reorganization of cellular microtubules.

A-10 cells were treated with laulimalide, isolaulimalide, or paclitaxel for 18 hours and the morphological effects on microtubules examined by indirect immunofluorescence techniques. The control cells exhibited normal microtubules arrays with filamentous microtubules radiating from the microtubule organizing center to the cell periphery. Treatment of the cells with laulimalide disrupted the normal microtubule array; the microtubules were more numerous and appeared to occupy more of the cytoplasm. A 2 μM laulimalide exhibited bundles of short tufts of microtubules that were prevalent in the cell periphery and seemed to be independent of nucleation from microtubule organizing centers. Isolaulimalide at concentrations between 2-20 μM caused an increase in the density of cellular microtubules, but no microtubule bundles were present. Paclitaxel at concentrations between 1-20 μM initiated the formation of a highly organized array of microtubules, some of which formed thick microtubule bundles. Long thick microtubule bundles often surrounded the nucleus. The extensive long microtubule hoops and bundles that formed after treatment with 2 μM paclitaxel were not seen with laulimalide. Cellular microtubules stabilized with paclitaxel, laulimalide or isolaulimalide were resistant to vinblastine-induced depolymerization.

Effects of Laulimalide and Isolaulimalide on Nuclear Structure

A characteristic of both A-10 and SK-OV-3 cells treated with a wide range of concentrations of laulimalide and isolaulimalide was the formation of multiple micronuclei. The effects of laulimalide on nuclear structure are visible: The normal rounded shape of the nucleus, which is devoid of microtubules, can be detected, whereas in laulimalide-treated cells this distinct microtubule-free area containing the discrete central nucleus was lost and only vesicle-like areas devoid of microtubules remained. Nuclear staining of control cells revealed a central compact nucleus, whereas laulimalide-treated cells exhibited a dramatic breakdown of the nucleus into micronuclei. Similar nuclear changes occurred with isolaulimalide. Paclitaxel also initiated the formation of micronuclei, as has been reported by others. Analysis of the incidence of micronuclei formation showed that a higher percentage of laulimalide-treated cells contained micronuclei than cells treated with the same concentrations of paclitaxel.

Figure 1:
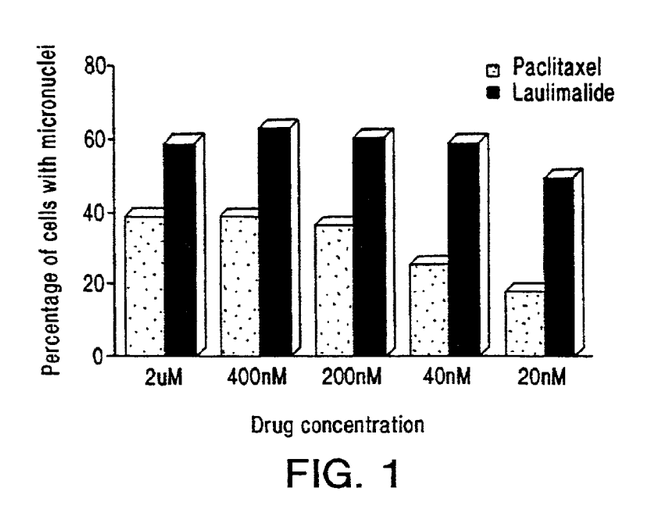
FIG. 1 is a graphic representation comparing the effects of Laulimalide and paclitaxel on micronuclei formation, in which A-10 cells were treated for 18 hours with Laulimalide or paclitaxel, the cells were fixed and nuclei were visualized by DAPI staining.

The data in FIG. 1 demonstrate that 0.02-2 μM laulimalide caused micronuclei formation in approximately 60% of A-10 cells. Paclitaxel at the same concentrations caused approximately 40% of the cells to exhibit this abnormal restructuring of the nucleus. At all concentrations tested, laulimalide caused a higher percentage of cells to exhibit micronuclei when compared with paclitaxel-treated cells. The difference between the two drugs was statistically significant at all five concentrations tested ($P<0.0001$).

Effects of Laulimalide on Cell Cycle Progression and Mitotic Spindles

Figure 2A:
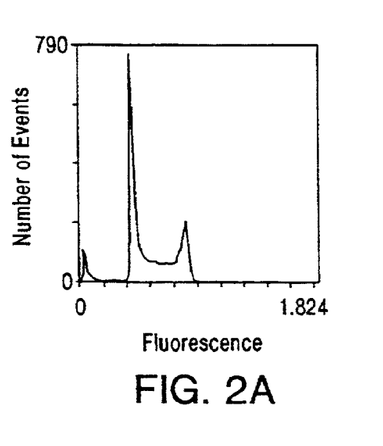
FIG. 2A portrays the control cells.
Figure 2B:
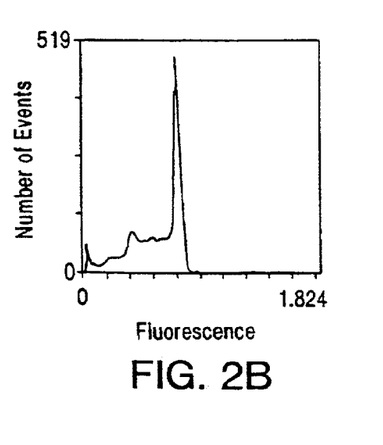
FIG. 2B portrays the cells treated with 20 nm Laulimalide for 9 hours.
Figure 2C:
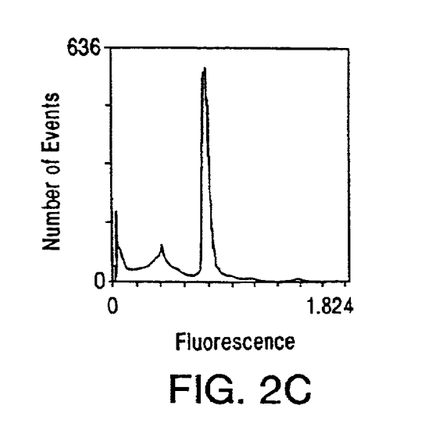
FIG. 2C portrays the cells treated with 20 nm Laulimalide for 18 hours.

A common characteristic of anti-microtubule agents is their ability to initiate mitotic arrest. Flow cytometric analysis revealed that laulimalide-induced cell cycle arrest in $G_2$-M in MDMB-435 breast carcinoma cells within nine hours of treatment (FIG. 2). This is consistent with the effects of other antimicrotubule agents, where disruption of microtubule dynamics prevents normal mitotic progression and leads to mitotic arrest. Abnormal mitotic spindles were seen in both A-10 cells and SK-OV-3 cells after treatment with laulimalide and isolaulimalide. The mitotic cells were rounded, and the spindles formed a circular pattern with spindle microtubules radiating outward from a microtubule-free core in the center of the cell. In the mitotic cells, the nuclear membranes were not apparent, and the chromatin was condensed and aligned in a circular pattern. Abnormal mitotic spindles were visible in paclitaxel-treated cells and were typically tri-or tetra-polar and did not exhibit the morphology seen with the laulimalides.

Effects of Laulimalide, Isolaulimalide, and Paclitaxel on Cell Proliferation of Drug-Sensitive and Multidrug-Resistant Cell Lines The early literature on laulimalide reported that it was a cytotoxin, but without specifying a mechanism. Experiments were conducted to determine the $IC_{50}$ values for laulimalide and isolaulimalide in two drug-sensitive cell lines, MDA-MB-435 and SK-OV-3, and in a multidrug-resistant cell line, SKVLB-1. Cells were treated with varying concentrations of the drugs for 48 hours, and cell-associated protein was determined using the SRB assay. The $IC_{50}$ for each compound was calculated for each cell line.

Laulimalide was found to be a potent inhibitor of cell proliferation with $IC_{50}$ values between 5-12 nM (Table 1).

TABLE 1

| Cell Line | Laulimalide | Isolaulimalide | Paclitaxel |
|---|---|---|---|
| MDA-MB-435 | 5.74 ± 0.58 | 1,970 ± 97 | 1.02 ± 0.25 |
| SK-OV-3 | 11.53 ± 0.53 | 2,570 ± 290 | 1.71 ± 1.07 |
| SKVLB | 1,210 ± 490 | 2,650 ± 1,384 | >100,000 |
| Resistance Factor | 105 | 1.03 | >58,480 |

The values represent the means of three (laulimalide, isolaulimalide) or four (paclitaxel) experiments ± SD Isolaulimalide is less potent with $IC_{50}$ values in the low μM range. Both laulimalide and isolaulimalide inhibited the proliferation of the SKVLB-1 cell line that overexpresses the drug efflux pump P-glycoprotein. The resistance factors between the parental, drug-sensitive line (SK-OV-3) and the drug-resistant cell line (SKVLB-1) were 105 and 1.03 for laulimalide and isolaulimalide, respectively (Table 1). Greater than 70% inhibition of the SKVLB-1 cell line was not achieved with concentrations of paclitaxel up to 100 μM. Laulimalide and isolaulimalide are significantly more effective against the SKVLB-1 cell line than paclitaxel. These data confirm that these new agents are poor substrates for transport by P-glycoprotein.

The $IC_{50}$ for inhibition of proliferation was also determined in the A-10 cell line, a nontransformed line that was used to show the effects of microtubule-stabilizing agents on cellular structures. The $IC_{50}$ for laulimalide was 51 μM and for paclitaxel was 40 μM. The nontransformed A-10 cell line was much less sensitive to the inhibitory effects of both paclitaxel and laulimalide, illustrating the need to use micromolar concentrations in these cells to induce abnormal microtubules.

Initiation of Apoptosis by Laulimalide

The ultimate mechanism of action of many cytotoxic cancer chemotherapeutic agents is the initiation of pathways of gene and protein expression leading to apoptosis. Antimicrotubule drugs including paclitaxel, vinblastine, and cryptophycin 1 initiate apoptosis both in vitro and in vivo. The flow cytometry data (FIG. 2) show a doubling of the subdiploid peak at 18 hours (FIG. 2C), suggesting the initiation of apoptosis. The loss of cellular DNA is detected by the appearance of the subdiploid peak when apoptotic cells are analyzed by flow cytometry. Studies were undertaken to determine whether laulimalide initiates a gene-driven program of cellular suicide.

During apoptosis, specific cysteine proteases called the caspases are activated. Activation of the caspase cascade leads to the proteolytic degradation of specific cellular proteins. The activation of caspase 3 and the proteolysis of the DNA repair enzyme PARP, a downstream substrate of caspase 3, were examined in cell lysates from laulimalide-treated cells. Activation of caspase 3 leads to the loss of the 32 kDa proenzyme and the formation of the activation products p17 and p12. Analysis of immunoblot data from cell lysates shows the formation of the p17 activation product at 24, 42 and 48 hours after laulimalide treatment. The loss of the p32 proenzyme is seen at 48 hours. The specific proteolysis of PARP by caspase 3 leads to the formation of two products, an 89 kDa COOH-terminal fragment and a 24 kDa N-terminal fragment. The proteolysis of PARP and the appearance of the 89 kDa degradation product coincided with the activation of caspase 3. Caspase 3 was activated and PARP proteolytically cleaved in cell lysates from cells treated with laulimalide for 42 and 48 hours. These data are consistent with laulimalide-induced apoptotic cell death.

Effects of Laulimalide on Tubulin Polymerization in Vitro

Figure 3A:
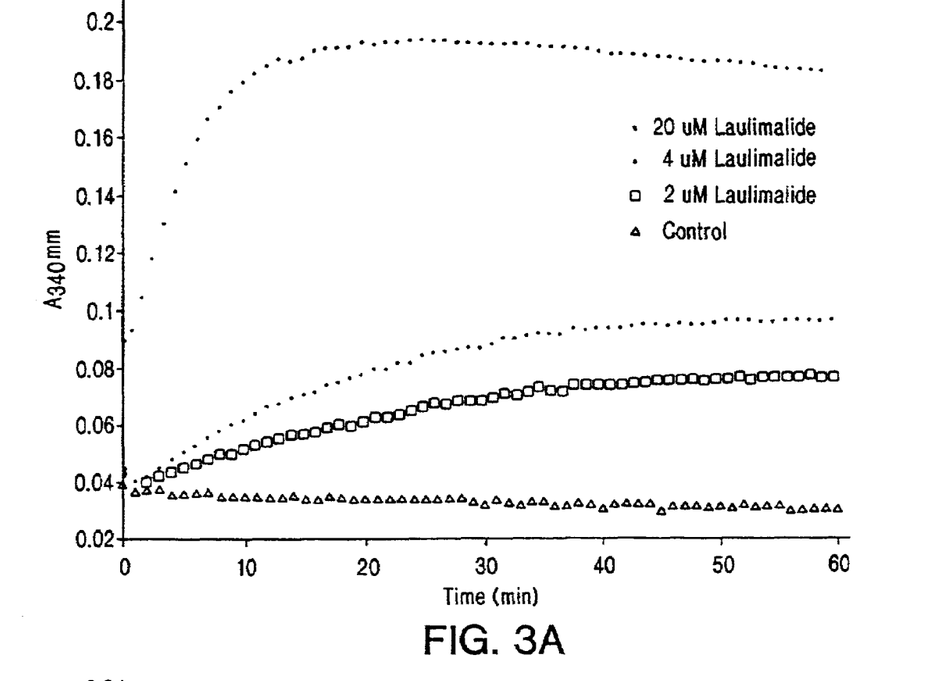
FIG. 3A portrays the cells treated with Laulimalide.
Figure 3B:
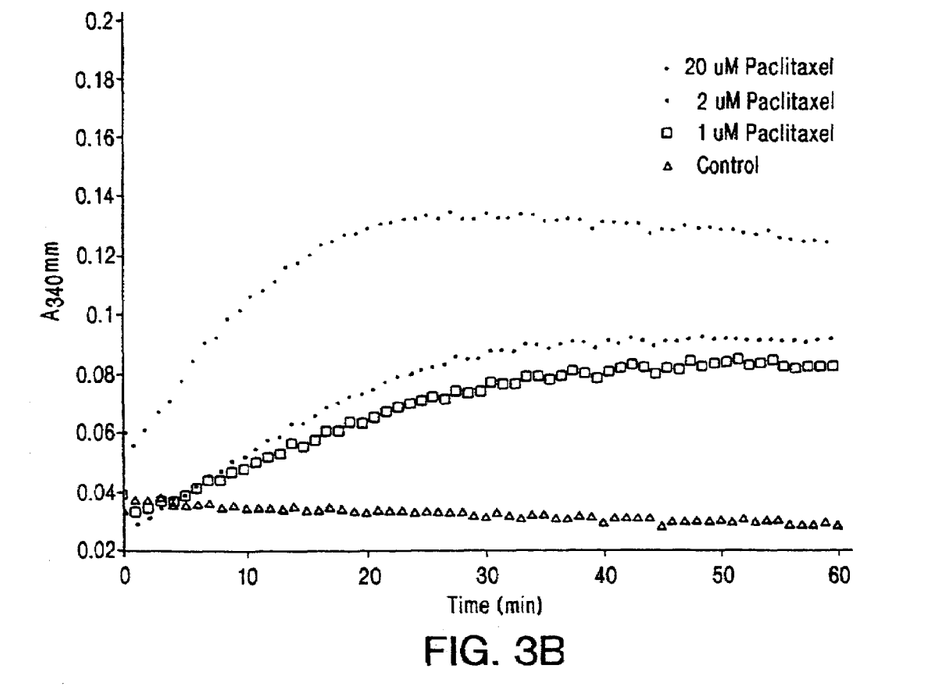
FIG. 3B portrays the cells treated with paclitaxel.

One characteristic of the microtubule-stabilizing agents paclitaxel, discodermolide, epothilones A and B, and eleutherobin is the ability of these agents to initiate the polymerization of tubulin in the absence of polymerization promoters, such as glycerol. Studies were undertaken to determine the effects of laulimalide on tubulin polymerization. Both isolaulimalide and laulimalide stimulated tubulin polymerization. FIG. 3A shows the effects of laulimalide on tubulin polymerization, and the accompanying FIG. 3B shows the effects of paclitaxel. Comparisons between the effects of laulimalide and paclitaxel on tubulin polymerization (FIG. 3, A and B) show that, at low micromolar concentrations, paclitaxel is more potent than laulimalide (see also Table 2).

TABLE 2

| Drug | $EC_{50}$ |
|---|---|
| Laulimalide | 4.32 ± 0.4 |
| Paclitaxel | 1.44 ± 0.06 |

At low micromolar concentrations more tubulin polymer was formed in the presence of paclitaxel, and the rate of polymerization was faster than was seen with equivalent concentrations of laulimalide.

A very different relationship was seen when comparing the 20 μM concentrations of laulimalide and paclitaxel. The 20 μM concentration of laulimalide was more effective at stimulating the formation of tubulin polymer than was the 20 μM concentration of paclitaxel (FIGS. 3A and 3B). Laulimalide promoted the polymerization of approximately 30% more tubulin polymer than was formed in the presence of paclitaxel, and the kinetics of tubulin formation were twice as fast as the rate measured in the presence of 20 μM paclitaxel.

The tubulin polymers that formed in the presence of laulimalide were insensitive to cold and $CaCl_2$-induced depolymerization. Neither paclitaxel nor laulimalide promoted the polymerization of tubulin at 0° C., and laulimalide stabilized tubulin polymer formed in the presence of GTP.

Samples of the tubulin polymer formed were examined by electron microscopy to determine whether the increase in turbidity measured during the polymerization experiments was due to the formation of microtubule-like polymers or the formation of other structures. Under high magnification (×63,000) the tubulin polymers formed by paclitaxel and laulimalide were indistinguishable. Both agents formed structures resembling tubules with evidence of longitudinal symmetry. Examination of tubulin polymers formed in the presence of the microtubule-stabilizing agents at lower magnification (×4,000) showed that the polymers formed with laulimalide were very long structures with rounded curves. The polymers formed with paclitaxel were notably shorter and exhibited no rounded curves, but instead formed linear structures with angular branches.

Laulimalide and isolaulimalide were first isolated on the basis of their cytotoxicity, however, the mechanism of action was not elucidated. These agents have now been shown to be paclitaxel-like stabilizers of microtubules that cause alterations of both interphase and mitotic microtubules. Laulimalide is a potent inhibitor of cell proliferation and initiates mitotic arrest, micronuclei formation, and ultimately apoptosis. These compounds are superior to paclitaxel in their ability to circumvent P-glycoprotein-mediated drug resistance. The laulimalides represent a new class of paclitaxel-like microtubule-stabilizing agents with properties that may provide advantages over the taxanes.

Laulimalide and isolaulimalide are chemically related compounds, with isolaulimalide being a decomposition product of laulimalide. The difference between these two compounds is in the size and attachment points of the oxygen-containing ring within the top portion of the molecules. Laulimalide contains a three-membered expocide ring involving carbons C-16 and C-17, whereas isolaulimalide contains a five-membered tetrahyddrofuran ring linking carbon C-17 with side chain carbon C-20. This slight chemical difference between laulimalide and isolaulimalide results in a difference in potency of greater than two orders of magnitude in their ability to inhibit cell proliferation. Furthermore, this site also seems to be crucial for recognition by the multidrug efflux pump P-glycoprotein. Laulimalide had a resistance factor of 105 when comparing the $IC_{50}$ values in SK-OV-3 cells and SKVLB-1 cells, whereas isolaulimalide was equally sensitive in both cell lines. These data demonstrate that the epoxide moiety of laulimalide is critical for its interaction with both tubulin and P-glycoprotein.

Among the five groups of known antimicrotubule agents having paclitaxel-like microtubule-stabilizing properties, laulimalide most closely resembles the epothilones. Although the ring size of laulimalide is two carbons larger (18-membered versus 16-membered), both contain a similar structural motif that incorporates the epoxide ring, an unsaturated side chain bearing a methylated heterocyclic ring, and the ester of the macrocyclic lactone ring. This similarity seems to translate to similar activities. Both stabilize microtubules, and like laulimalide, the epothilones are poor substrates for P-glycoprotein-mediated transport.

The cellular effects of laulimalide are similar to, but distinct from, the cellular effects of paclitaxel. The increase in the density of cellular microtubules observed at low concentrations of laulimalide closely resembled the changes induced by paclitaxel at the same concentrations. However, at concentrations above 2 μM, the effects diverged and laulimalide initiated short thick bundles of microtubules that were more prevalent in the cell periphery and appeared to form from many nucleation centers. These effects are consistent with the greater efficacy of 20 μM laulimalide in promoting the polymerization of purified tubulin. In contrast, paclitaxel-induced microtubule bundles were long and thick and aligned in the central areas of the cells surrounding the nucleus, consistent with nucleation from one or two centers. Long microtubule bundles were not seen in cells treated with a wide range of laulimalide concentrations. These data demonstrate that in cells, laulimalide was not as effective as paclitaxel at elongation of microtubules, but was more effective at stimulating the formation of microtubules from multiple nucleation centers, resulting in shorter microtubule bundles in the periphery rather than the long microtubule bundles surrounding the nucleus.

The microtubules that form the mitotic spindle are highly dynamic structures and are more sensitive to disruption by antimicrotubule agents than are the less dynamic interphase microtubules. Agents that target microtubules disrupt mitotic spindle dynamics, thereby preventing normal mitosis, leading to mitotic arrest. Mitotic spindles formed in the presence of laulimalide were abnormal and formed unique starburst arrays in contrast to the short thickened tri- and tetra-polar spindles formed in the presence of paclitaxel. Laulimalide-treated mitotic cells exhibited chromatin condensation, loss of the nuclear envelope and abnormal chromatin alignment. The aberrant mitotic spindles were associated with circular chromatin arrays, suggesting that the microtubules were coordinating a specific, but abnormal structuring of the chromatin. Disruption of the mitotic apparatus by laulimalide treatment lead to mitotic arrest, followed by the initiation of apoptosis, as determined by the increase in cells in $G_2$-M and the activation of the caspase cascade.

Cells treated with laulimalide exhibited vesicle-like structures in the central region of the cell. DAPI staining revealed that these structures were composed of DNA and that laulimalide initiated the formation of multiple micronuclei. In A-10 cells, micronuclei were found in the majority of cells with treatments of 20 nM-2 μM laulimalide. Micronuclei formations occur as a consequence of treatment with either paclitaxel or epothilones and are thought to be the result of abnormal mitosis leading to abnormal chromosome segregation.

One characteristic of the paclitaxel-like microtubule-stabilizing agents is their ability to promote the polymerization of tubulin. Normally tubulin will not polymerize without tubulin promoters; however, laulimalide, like paclitaxel, stimulated the polymerization of tubulin in the absence of microtubule-associated proteins and glycerol. The rate and extent of polymerization in the presence of laulimalide was dependent on concentration and differed significantly from paclitaxel, suggesting that there are differences in their mechanisms of action. Further experimentation in the presence of difference tubulin and laulimalide concentrations and in the presence and absence of microtubule-associated proteins will allow more comprehensive comparisons of the tubulin polymerizing effects of laulimalide as compared with paclitaxel, discodermolide, and the epothilones.

The tubulin polymers formed in the presence of laulimalide were indistinguishable from paclitaxel-induced polymers under high magnification, but were noticeably longer than the paclitaxel-induced polymers when visualized under lower magnification. Under these conditions, laulimalide seems to promote polymer-elongating activity more readily than paclitaxel. These in vitro effects with purified tubulin differ from the effects in cells where paclitaxel promotes longer microtubules, whereas laulimalide promotes short microtubules. The initial results demonstrate that there are intriguing differences in the mechanisms of action of laulimalide and paclitaxel.

The clinical success of the taxanes in treating a wide range of tumors has lead to the search for new agents with a similar mechanism of action. The recent discovery of the beneficial activities of the class of laulimalides provides new drugs which are expected to prove useful to treat cancer.

All patents and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

The invention claimed is:

1. A composition comprising a compound seleded from the group consisting of the following structures:

-continued and combinations thereof.

2. A composition according to claim 1, further comprising at least one anti-neoplastic agent.

3. A composition according to claim 2, wherein said at least one anti-neoplastic agent is selected from the group consisting of an anti-metabolite, an alkylating agent, a plant-derived natural product, an antibiotic, a hormone and an enzyme.

4. A composition according to claim 2, wherein said at least one anti-neoplastic agent is selected from the group consisting of a ymca alkaloid, a taxane, an eporhilone, discoderrnalide, eleutherobin and a sarcodictyin.

5. A method of inhibiting the proliferation of a hyperproliferative mammalian cell having a multiple drug resistant phenotype, wherein said hyperproliferative manimalian cell is selected from the group consisting of hyperproliferative mammary cells, hyperproliferative colorectal cells, leukemia cells, melanoma cells, pancreatic adenocarcinoma cells, hyperproliferative central nervous system (CNS) cells, hyperproliferative ovarian cells, hyperproliferative prostate cells, hyperproliferative gastric cells, hyperproliferative pancreatic cells, hyperproliferative esophageal cells, hyperproliferative stomach cells, myeloma cells, hyperproliferative bladder cells, hyperproliferative renal cells, and hyperproliferative neuroendocrine cells, said method comprising contacting the cell with an amount of a composition according to claim 1, wherein said amount is effective to disrupt the dynamic state of microtubule polymerization and depolyrnerization to arrest cell mitosis, thereby inhibiting the proliferation of the cell.

6. A method of treating hyperproliferating, multiple drug resistant mammalian cells, said method comprising administering to a subject an effective amount of the therapeutic composition according to claim 1, wherein said hyperproliferating, multiple drug resistant mammalian cells are selected from the group consisting of mammary, small-cell lung, non-small-cell lung, colorectal, leukemia, melanoma, pancreatic adenocarcinoma, central nervous system (CNS), ovarian, prostate, sarcoma of soft tissue or bone, head and neck, gastric, pancreatic, esophageal, stomach, myeloma, bladder, renal, neuroendocrine, thyroid, non-Hodgkin's disease and Hodgkin's disease neoplasms.

7. A method according to claim 6, further comprising administering to the subject at least one additional therapy.

8. A method according to claim 7, wherein said at least one additional therapy is selected from the group consisting of chemotherapy, surgery, radiation therapy, therapy with biologic response modifiers and immunotherapy.

9. A method according to claim 6, wherein said hyperproliferating, multiple drug resistant mammalian cells are selected from the group consisting of mammary, ovarian, and prostate.

10. The composition of claim 1 wherein said compound is

R = CH₂OCH₃

11. The composition of claim 1 wherein said compound is

12. The composition of claim 1 wherein said compound is

13. The composition of claim 1 wherein said compound is

14. The composition of claim 1 wherein said compound is

15. The composition of claim 1 wherein said compound is

* * * * *

UNITED STATES PATENT AND TRADEMARK OFFICE
CERTIFICATE OF CORRECTION

PATENT NO. : 7,435,754 B2
APPLICATION NO. : 10/126674
DATED : October 14, 2008
INVENTOR(S) : Susan L. Mooberry and Bradley S. Davidson It is certified that error appears in the above-identified patent and that said Letters Patent is hereby corrected as shown below:

Claim 1, column 20, line 51, "compound seleded", should read --compound selected--

Claim 4, column 22, lines 24-25, "ymca alkaloid, a taxane, an eporhilone, dicoderrnalide" should read --vinca alkaloid, a taxane, an epothilone, dicodermalide--

Claim 5, column 22, line 28, "manimalian", should read --mammalian--

Claim 10, column 23, line 5, "Si(I-Pr)", should read --Si(i-Pr)3--

Claim 11, column 23, line 21, "Si(I-Pr)", should read --Si(i-Pr)3--

Signed and Sealed this

Second Day of June, 2009

JOHN DOLL
*Acting Director of the United States Patent and Trademark Office*